United States Patent [19]

Heimke

[11] 4,184,213
[45] Jan. 22, 1980

[54] ARTICULATORY ENDOPROSTHESES OF NONMETALLIC MATERIALS

[76] Inventor: Gunther Heimke, Zinkgräfstrasse 62, Weinheim, Fed. Rep. of Germany, D-6940

[21] Appl. No.: 915,779

[22] Filed: Jun. 15, 1978

[30] Foreign Application Priority Data

Jul. 21, 1977 [DE] Fed. Rep. of Germany ....... 2732923

[51] Int. Cl.² ............................................. A61F 1/24
[52] U.S. Cl. ........................................ 3/1.91; 3/1.912; 128/92 C
[58] Field of Search .................................. 3/1.9–1.913; 128/92 C, 92 CA

[56] References Cited

U.S. PATENT DOCUMENTS

| 3,924,275 | 12/1975 | Heimke et al. ..................... 3/1.912 |
| 4,012,795 | 3/1977 | Doore et al. ..................... 3/1.913 X |
| 4,031,571 | 6/1977 | Heimke et al. ..................... 3/1.913 |

FOREIGN PATENT DOCUMENTS

| 2134316 | 1/1972 | Fed. Rep. of Germany ............ 3/1.913 |
| 2324865 | 11/1974 | Fed. Rep. of Germany ............ 3/1.913 |
| 2451275 | 5/1976 | Fed. Rep. of Germany ............ 3/1.913 |
| 2461339 | 7/1976 | Fed. Rep. of Germany ............ 3/1.913 |

Primary Examiner—Ronald L. Frinks
Attorney, Agent, or Firm—Fisher, Christen & Sabol

[57] ABSTRACT

An articulatory endoprosthesis having bearing surfaces of dense aluminum oxide ceramic are provided with anchoring elements formed from hot-pressed compounds of silicon with carbon and/or nitrogen having a bending strength of more than 600 N/mm²; preferred compositions comprise silicon nitride and silicon carbide.

3 Claims, 1 Drawing Figure

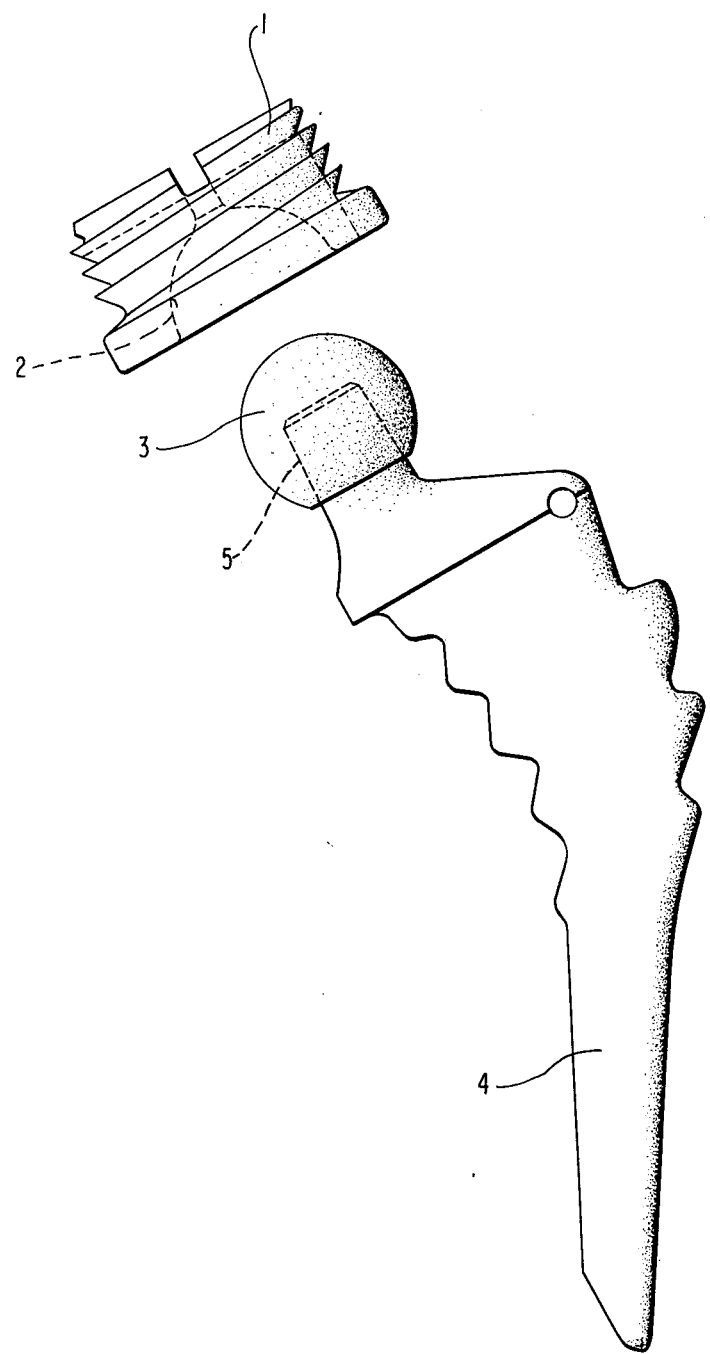

ARTICULATORY ENDOPROSTHESES OF NONMETALLIC MATERIALS

This invention concerns articulatory endoprostheses, in particular for the highly-stressed parts of the motor apparatus, having dense aluminum oxide ceramic along the articulating surfaces of the joint.

Articulatory endoprostheses generally serve as replacements for joints of the human motor apparatus that have been damaged by disease or accident. In earlier forms of execution of such articulatory endoprostheses the articulating surfaces consisted either of metal or of a combination of metal and plastic. Prostheses with the frictional combination of metal against metal have been used less and less in recent years, for in this case the friction coefficient is relatively high and also large quantities of grindings are produced. These metallic grindings are very poorly tolerated by the body. The endoprostheses used to the greatest extent at present use a combination of certain types of polethylene and metal as frictional components. The grindings that arise in this combination are primarily of polyethylene and are considerably less damaging to the body than the previously mentioned metal grindings. However, on the one hand this grinding is so great that the removal of polyethylene that it causes makes replacement of the prosthesis necessary after at most 10 to 15 years, and on the other hand it can be shown that this wear on the polyethylene contributes to certain loosening phenomena of the individual components of such prostheses in the bone area bordering the joint.

Such wear phenomena on the articulating surfaces of the prostheses is avoided when both frictional components are manufactured of high-density, high-strength aluminum oxide ceramic. Such a construction is described, for example, in German disclosure DOS No. 2,134,316.

However, even such prostheses still use metal components, wholly or in part, for the anchoring of the articulatory endoprostheses in the skeletal parts or bone areas adjacent to the joint. In this case these metal parts are anchored in this bone area using plastic bone cement, which consists of methyl methacrylate, or they are implanted without cement. In the first case the full mechanical strength of the metal cannot be exploited, for the moduli of elasticity of the metals employed admit such deformation of these metal parts under higher loads that the strength of the surrounding cement is exceeded resulting in fracture of the surrounding cement. Such a fracture, which initially need be only a very fine fissure, in the surrounding of a metal prosthesis, e.g. in the plastic-cement sheath enclosing the shaft portion of the upper-thigh component of a total-hip endoprosthesis, with further load cycles leads inevitably to such severe damage that the prosthesis must be replaced. — If the components of articulatory endoprostheses are anchored directly, i.e. without the utilization of the above-mentioned plastic bone cement, in the bone area adjacent to the joint, then because of only limited biological tolerance of metals after a few years loosening phenomena appear in a high percentage of cases that similarly force the replacement of the prosthesis in the end. In the last-named case one can give the prosthetic parts larger dimensions and thus make them more stable in form, but still in these direct, cement-free anchorings the causes of the loosening lie not so much in the deformation of the prosthesis as in the limited tolerance of the metals employed, as already mentioned.

— Attempts have been made recently in the case of metal parts to be implanted with cement as well, to keep the deformation occurring under higher loads smaller by enlarging, for example, the shafts of the upper-thigh components of total hip endoprostheses. In many cases, however, such prostheses can still hardly be implanted, and further the cement sheath that remains becomes so thin that there is therewith induced a danger of fracture.

The object of the invention is then to solve this anchoring problem. The problem may be made more precise and can be divided into two sub-problems: on the one hand, for the case of anchoring with plastic bone cement a means of anchoring must be found that while exhibiting the same fatigue strength as the best of the previously-employed metals has less deformation than the plastic bone cement surrounding the prosthesis, and on the other hand, for the case of cement-free cementless implantation, there must be such good bodily tolerance that a dense growth of load-bearing bone structures suitable for the acceptance and transfer of the load, is ensured on the surface of the implant.

This task is accomplished in accordance with the invention in that the parts serving in the anchoring of the prosthesis consist of hot-pressed compounds of silicon with carbon and/or nitrogen having a bending strength of over 600 N/mm$^2$.

Hot-pressed compounds of silicon with carbon and/or nitrogen belong to the class of hard materials. Their modulus of elasticity is over ten times as high as the modulus of elasticity of the metal alloys used hitherto for prosthetic purposes, which were based on stainless steels or cabalt-chromium-molybdenum alloys. The bending strength of over 600 N/mm$^2$ mentioned above is the static bending strength of these silicon compounds. In investigations simulating conditions inside the body, however, it was possible to show that with these materials the decrease in strength as a function of the load cycle is very small. Even after 10 million load cycles with bending stresses higher than those normally occuring in prostheses only 25% decrease in the strength was found, i.e. to about 450 N/mm$^2$. Further, our own investigations using animals show that this material exhibits a favorable tolerance in the body similar to that known for a long time in dense, high-purity aluminum oxide ceramic.

The above-mentioned strength tests and the compatibility studies were carried out on hot-pressed solicon nitride of the composition $Si_3N_4$. The parts serving in particular for the anchoring of the articulatory endoprostheses can therefore be composed of this material.

The parts serving for the anchoring of articulatory endoprostheses, however, can also advantageously consist of silicon carbide (SiC). This material as well has advantageous properties like the above-mentioned silicon nitride.

The prosthetic parts for anchoring in accordance with the invention must of course be formed in each individual case in accordance with the biomechanical circumstances of the joint components of that case and also must be formed as much as possible in a manner appropriate to the material. For the femur components of hip endoprostheses, in the case of anchoring with a plastic bone cement, a form in accordance with German Pat. No. P 2527569 can be considered. If this joint component is implanted without cement then forms such as those in German Pat. No. 2,324,865 or in German disclosures DAS No. 24 61 339 or DAS No. 24 17 702 can be used.

For the forming of such prostheses various processes are available that are known to the expert in the field. For the most recent process we would refer to German patent application Nos. P 26 47 651 and P 26 56 761.

In the single FIGURE there is represented as an articulatory endoprosthesis according to the invention, a total hip endoprosthesis.

Here the socket 1 consists of dense, high-strength $Al_2O_3$ ceramic with an approximately hemispherical recess 2, the surface of which is finely polished. In the implanted and functional state there is situated in this the head portion 3 of the femur component. This head part is essentially spherical and its surface is finely polished. These two highly polished surfaces form the articulating surfaces of the joint. For the anchoring of the ball 3 replacing the femur head, in the narrow space of the femur the shaft 4 is used. In the example represented here it has the form of a notched shaft that is intended for anchoring without cement. The connection between the ball 3 and the shaft 4 serving in the anchoring can be effected, as in the example shown, by means of the self-locking cone 5. In accordance with the invention the shaft 4 consists of the hot-pressed compound of silicon with carbon and/or nitrogen, e.g. of silicon carbide (SiC) or silicon nitride ($Si_3N_4$).

I claim:

1. Articulatory endoprostheses, in particular for the highly-stressed parts of the motor apparatus, with dense aluminum oxide ceramic along the articulating surfaces of the joint, characterized in that the parts serving for the anchoring of the prostheses consist of hot-pressed compounds of silicon with carbon and/or nitrogen that exhibit a bending strength of more than 600 N/mm$^2$.

2. Articulatory endoprostheses according to claim 1, characterized in that the parts serving for the anchoring consist of silicon nitride with the composition $Si_3N_4$.

3. Articulatory endoprostheses according to claim 1, characterized in that the parts serving for the anchoring consist of silicon carbide (SiC).